United States Patent [19]

Verbrugge et al.

[11] 4,247,711

[45] Jan. 27, 1981

[54] PREPARATION OF 2-FORMYL-3,3-DIMETHYLCYCLO-PROPANEACETIC ACID

[75] Inventors: Pieter A. Verbrugge; Petrus A. Kramer, both of Amsterdam, Netherlands

[73] Assignee: Shell Oil Company, Houston, Tex.

[21] Appl. No.: 32,848

[22] Filed: Apr. 24, 1979

[30] Foreign Application Priority Data

May 2, 1978 [GB] United Kingdom ............... 17268/78
May 2, 1978 [GB] United Kingdom ............... 17269/78

[51] Int. Cl.$^3$ .................... C07C 69/67; C07C 59/147; C07C 49/553; C07C 49/583
[52] U.S. Cl. .................... 560/124; 568/303; 568/343; 568/374; 562/506
[58] Field of Search .................... 562/506; 560/124; 260/586 C, 586 P

[56] References Cited

U.S. PATENT DOCUMENTS 3,637,823  1/1972  Berg .................................... 562/506

FOREIGN PATENT DOCUMENTS 43-22592  9/1968  Japan .................................... 562/506

*Primary Examiner*—Natalie Trousof
*Assistant Examiner*—Michael Shippen

[57] ABSTRACT

2-Formyl-3,3-dimethylcyclopropylacetic acid is prepared by ozonolysis of 3-acetyl-6,6-dimethylbicyclo[3.1.0]-2-hexene followed by reductive cleavage of the ozonolysis product thus formed. The 3-acetyl-6,6-dimethylbicyclo[3.1.0]-2-hexene is prepared by contacting 2-(2-acetyl-3-oxobutyl)-3,3-dimethylcyclopropanecarbaldehyde with a base in the presence of a solvent.

43 Claims, No Drawings

PREPARATION OF 2-FORMYL-3,3-DIMETHYLCYCLOPROPANEACETIC ACID

BACKGROUND OF THE INVENTION

1. Field of the Invention

The present invention relates to a process for the preparation of 2-formyl-3,3-dimethylcyclopropaneacetic acid and intermediates thereof.

2. Description of the Prior Art

U.S. Pat. No. 3,708,528 describes the ozonolysis of 4-acetyl-2-carene, followed by reductive cleavage of the ozonolysis product thus formed to yield 2-(2-acetyl-3-oxobutyl)-3,3-dimethylcyclopropanecarbaldehyde having the formula

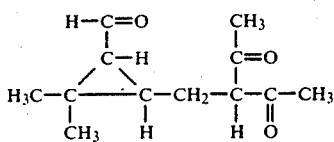

also named hereinafter "compound A".

Applicants have found a simple process to convert this compound A, into other valuable intermediates in the preparation pyrethroid pesticides.

SUMMARY OF THE INVENTION

Accordingly, the invention provides a process for the preparation of 3-acetyl-6,6-dimethylbicyclo[3.1.0]-2-hexene, which comprises contacting 2-(2-acetyl-3-oxobutyl)3,3-dimethylcyclopropanecarbaldehyde with a base in the presence of a solvent.

The compound 3-acetyl-6,6-dimethylbicyclo[3.1.0]-2-hexene having the formula

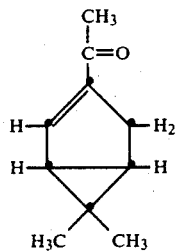

also named hereinafter "compound B", is the useful intermediate in the preparation of pyrethroids referred to hereinbefore.

Examples of bases which can be used in the process according to the invention are alkali metal hydroxides, alkali metal alkoxides and alkaline earth metal hydroxides, tertiary amines such as the trialkylamines in U.S. Pat. No. 4,169,105, quaternary ammonium bases such as described in U.S. Pat. No. 3,110,362 and basic ion exchangers. Very suitable bases are alkali metal alkoxides, particularly those with fewer than five carbon atoms per molecule, for example, sodium methoxide and potassium methoxide and alkali metal hydroxides, for example, sodium hydroxide and potassium hydroxide.

Suitably at least the stoichiometric amount, but preferably between about 1.0 and about 2.5 times the stoichiometric amount of base is used, however; the use of less than the stoichiometric amount of base is not precluded. In determining this stoichiometric amount compound A is regarded as a monovalent acid.

Examples of solvents which can be used in the process according to the invention are alkanols, carbon tetrachloride, dichloromethane, tetrahydrofuran, alkanes with 5 to 10 carbon atoms per molecule, acetone, diethyl ether and N,N-dimethylformamide. Alkanols, particularly those with fewer than five carbon atoms per molecule such as methanol, are particularly useful.

The process according to the invention may be carried out at mild temperatures, for example, between about 0° C. and about 125° C., but temperatures outside this range are not precluded. Ambient temperature is usually very suitable.

It has been found that the preparation of compounds A and B can be carried out in the same reaction zone or vessel. It is this aspect that greatly simplifies the preparation of the intermediate compound B in the synthesis of the above-mentioned important insecticides. Thus, compound A has been prepared by ozonolysis of 4-acetyl-2-carene followed by reductive cleavage of the ozonolysis product thus obtained and compound A thus prepared has been contacted with a base in the presence of a solvent in the same reaction zone or vessel as the said ozonolysis and reductive cleavage.

Starting from the (+) and (−) configuration of 4-acetyl-2-carene one obtains the (+) and (−) configurations of compound B, respectively.

The solvents mentioned hereinbefore for the conversion of compound A into compound B may also be used for the said ozonolysis and reductive cleavage. This provides the possibility of using the same solvent throughout; preferably use is made of an alkanol with fewer than five carbon atoms per molecule, particularly methanol. The ozonolysis of 4-acetyl-2-carene in the presence of an alkanol must be carried out in the presence of a compound preventing acetalization of the formyl group in compound A by reaction with the alkanol. A base may be used to prevent acetal formation; this base may be different from, but is preferably the same as, that used in the subsequent preparation of compound B. The amount of base needed to prevent acetal formation is very small, for example between 0.05 and 10% m, calculated on 4-acetyl-2-carene. This provides the possibility of using a very small amount of base in the ozonolysis of 4-acetyl-2-carene and supplying more of this base after the reductive cleavage of the ozonolysis product to effect the conversion of compound A into compound B. However, if desired, the amount of base required for the conversion of compound A into compound B may already be present during the ozonolysis and reductive cleavage. In the latter case compound A is converted in situ into compound B.

When, according to U.S. Pat. No. 3,708,528, 4-acetyl-2-carene is treated with a gaseous mixture containing ozone and oxygen and the ozonolysis product thus formed is subjected to reductive cleavage, compound A is formed in a low yield. However, according to copending allowed U.S. patent application Ser. No. 14,529, filed Feb,. 23, 1979 ozonolysis of 4-acetyl-2-carene in the presence of an anti-oxidant affords compound A in an attractively high yield. The anti-oxidant may be a sterically hindered phenol, i.e. a phenol having as ortho substituent(s) (a) secondary and/or (a) tertiary hydrocarbyl group(s). Examples of such groups are isopropyl, tert-butyl, tert-pentyl, cyclohexyl, norbonyl and isobornyl groups.

The sterically hindered phenols may be mononuclear or polynuclear. Examples of mononuclear phenols are 2,6-di-tert-butylphenol, 2,6-di-tert-butyl-4-methylphenol, 2,4-di-tert-butyl-6-methylphenol, 2,6-diisopropyl-4-methoxymethylphenol; 2,6-di-tert-butyl-4-hydroxymethylphenol, 2,4-dimethyl-6-tert-butylphenol, 2,4,6,tri-tert-butylphenol, 2,6-dicyclohexyl-4-methylphenol, 2,6-dimethyl-4-cyclohexylphenol; 4-methyl-2,6-dioctadecylphenol, 6-(1,1-dimethylhexyl)-2,4-dimethylphenol and 2,6-di-tert-butyl-4-methoxymethylphenol. Examples of polynuclear phenols are biphenols, such as 3,3′,5,5′-tetra-tert-butyl-4,4′-dihydroxybiphenyl and 3,3′5,5′-tetraisopropyl-4,4′-dihydroxybiphenyl, and biphenols such as bis(3,5-di-tert-butyl-4-hydroxyphenyl)methane, bis(3-tert-butyl-2-hydroxy-5-methylphenyl)methane and 2,2-di(3,5-di-tert-butyl-4-hydroxyphenyl)propane. Other polynuclear phenolic compounds which can be used in the process according to the invention include the 4,4′-di(3,5-dialkyl-4-hydroxybenzyl)-2,2′,3,3′5,5′6,6′-octamethylbiphenyls, such as 4,4′-di(3,5-di-tert-butyl-4-hydroxybenzyl)-2,2′,3,3′,5,5′,6,6′-octamethylbiphenyl, polyphenolic phenols such as 1,3,5-trimethyl-2,4,6-tri-(3,5-di-tert-butyl-4-hydroxybenzyl)benzene, 2,4,6-tri(3,5-di-tert-amyl-4-hydroxybenzyl)phenol and 1,1,3-tri(5-tert-butyl-4-hydroxy-3-methylphenyl)butane, and di-(3,5-dialkyl-4-hydroxybenzyl)polynuclear aromatics, such as 9,10-di(3,5-di-tert-butyl-4-hydroxybenzyl)anthracene and 1,4-di(3,5-diisopropyl-4-hydroxybenzyl)naphthalene.

The anti-oxidant used in the process according to the invention may be a derivative of an aromatic amine, such as 1,4-di(sec-butylamino)benzene, N-(4-isopropylaminophenyl)aniline, 1,4-dianilinobenzene, 1-anilinonaphthalene and 2-anilinonaphthalene.

The anti-oxidant may be a heterocyclic compound, such as 6-ethoxy-2,2,4-trimethyl-1,2-dihydroquinoline, 10,10-dimethyl-9,10-dihydroacridine, benzimidazol, 2-mercaptobenzimidazol and phenothiazine.

The required amount of anti-oxidant usually varies from about 0.001 to about 10% m, based on the starting amount of 4-acetyl-2-carene. However, amounts outside this range are not precluded.

The ozonolysis may be carried out at a temperature below about −50° C., but in the presence of an anti-oxidant such extremely low temperatures are not necessary. Temperatures in the range of from about −20° C. to about +20° C., and particularly from about 0° C. to 15° C., are very suitable.

The gaseous mixture comprising ozone and oxygen may, if desired, be diluted with an inert gas, for example, nitrogen, air or argon.

The reductive cleavage of the ozonolysis product to compound B may be carried out with one or more of the many reducing agents known in the art. This reduction may be carried out cataytically, for example, with hydrogen in the presence of a reduction catalyst. Examples of reduction catalyst are noble metals of Group VIII of the Periodic Table of the Elements, supported on a carrier, such as platinum supported on carbon. Other examples of reducing agents are dimethyl sulphide, potassium iodide, stannous chloride and formaldehyde; sodium bisulphite is a useful reducing agent in cases where the aldehyde formed is to be isolated.

The invention further provides a process for the preparation of 2-formyl-3,3-dimethylcyclopropylacetic acid, which comprises ozonolysis of 3-acetyl-6,6-dimethylbicyclo-[3.1.0]-2-hexane (compound B) followed by reductive cleavage of the ozonolysis product thus formed.

The compound 2-formyl-3,3-dimethylcyclopropylacetic acid having the formula

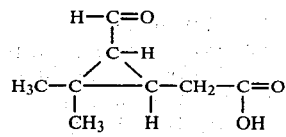

also named hereinafter "compound C", is the intermediate in the preparation of the pyrethroids referred to hereinbefore. It will be seen that compound C has two asymmetric carbon atoms. The nomenclature used to describe the spatial configurations of the four possible isomeric forms is the so-called Elliot nomenclature as defined by M. Elliott, A. W. Farnham, N. F. Janes, P. H. Needham and D. A. Pulman in Nature, 1974, 248, 710. Starting from the (+) configuration of compound B one obtains compound C exclusively in the 1R,cis configuration. This is of great advantage, because among the spatial configurations of the above-mentioned pyrethroids the 1R,cis configuration has the highest pesticidal activity.

The ozonolysis can be carried out at a temperature which is not critical and may vary within wide limits, but at temperatures below about −25° C. the reaction mixture obtained after the reductive cleavage contains compound C in very small amounts only, the novel compound 2,2-dimethyl-3-(2,3-dioxobutyl)cyclopropanecarbaldehyde having the formula

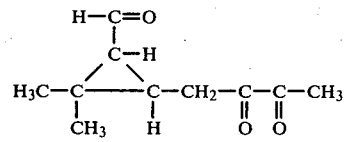

also named hereinafter "compound D", being present in appreciable quantities. Ozonolysis of compound B at temperatures above −25° C. affords compound C in an acceptable yield; therefore, the ozonolysis is preferably carried out at a temperature in the range of from about −25° C. to about +30° C. and particularly of from about −5° C. to about +20° C.

The gaseous mixture comprising ozone and oxygen may, if desired, be diluted with an inert gas, for example nitrogen, air or argon.

The reductive cleavage of the ozonolysis product may be carried out with one or more of the many reducing agents known in the art. This reduction may be carried out catalytically, for example, with hydrogen in the presence of a reduction catalyst. Examples of reduction catalysts are noble metals of Group VIII of the Periodic Table of the Elements, supported on a carrier, such as platinum supported on carbon. Other examples of reducing agents are dimethyl sulphide, potassium iodide, stannous chloride and formaldehyde; sodium bisulphite is a useful reducing agent in cases where the aldehyde formed is to be isolated.

Very good yields of compound C are usually obtained when the reaction is carried out in the presence of an alkanol as a solvent. The use of an alkanol provides the possibility of obtaining a dialkyl acetal of compound C as an end product, which is also within the scope of the present invention. In cases where compound C itself is the desired end product and an alkanol is used as a solvent a compound preventing acetal formation is suitably used. Examples of compounds, preventing acetal formation are basic compounds, such as alkali metal carbonates, alkali metal alcoholates and amines, for example potassium carbonate, sodium methoxide and pyridine. Examples of alkanol solvents are methanol, ethanol, propanol and 2-propanol. Very good results have been obtained with methanol.

Examples of other solvents in which the process according to the invention may be carried out are carbon tetrachloride, chloroform, dichloromethane, methyl chloride, ethyl chloride, ethyl acetate, tetrahydrofuran, nitromethane, alkanes with 5 to 10 carbon atoms per molecule, acetone and diethyl ether.

It has been found that the preparation of compounds A, B and C can be carried out in the same reaction zone or vessel. It is this aspect that greatly simplifies the preparation of the intermediate compound C in the synthesis of the above-mentioned important insecticides. Thus, compound B has been prepared by ozonolysis of 4-acetyl-2-carene, reductive cleavage of the ozonolysis product thus obtained with formation of compound A and contacting of compound A with a base in the presence of a solvent with formation of compound B, all of these reactions being carried out in the same reaction zone or vessel.

The solvents mentioned hereinbefore for the ozonolysis of compound B and the reductive cleavage of the ozonolysis product thus formed may also be used for the said preparation of compounds A and B. This provides the possibility of using the same solvent in the preparation of compounds A, B and C; preferably use is made of an alkanol with fewer than five carbon atoms per molecule, particularly methanol. The ozonolysis of 4-acetyl-2-carene in the presence of an alkanol must be carried out in the presence of a compound preventing acetalization of the formyl group in compounds A and C by reaction with the alkanol. A base may be used to prevent formation; this base is preferably the same as that used for the preparation of compounds A, B and C, but, if desired, different bases may be used. The amount of base needed to prevent acetal formation is very small, for example between 0.05 and 10% m, calculated on 4-acetyl-2-carene. This provides the possibility of using a very small amount of base in the ozonolysis of 4-acetyl-2-carene and supplying more of this base after the reductive cleavage of the ozonolysis product to effect the conversion of compound A into compound B. However, if desired, the amount of base required for the conversion of compound A into compound B may already be present during the ozonolysis and reductive cleavage. In the latter case compound A is converted in situ into compound B. Preferably, ozonolysis of 4-acetyl-2-carene and compound B are carried out in the presence of the same anti-oxidant.

2-Formyl-3,3-dimethylcyclopropylacetic acid, alkyl esters, salts and dialkyl acetals thereof are the novel compounds referred to hereinbefore. These alkyl esters and dialkyl acetals preferably have fewer than five carbon atoms per alkyl group, the methyl ester and the dimethyl acetal being preferred. Salts contain as the salt-forming cation an alkali, alkaline earth, aluminum, heavy metals, ammonia or tetrahydrocarbylammonium in which the total carbon atoms in the hydrocarbyl groups are between 4 and 70.

The compounds of the present invention are useful intermediates in the synthesis of pyrethroid pesticides. For example, the methy 2-formyl-3,3-dimethylcyclopropaneacetate may be converted into 2-(2,2-dihalovinyl-3,3-dimethylcyclopropanecarboxylic acids as described in concurrently filed U.S. patent application Ser. No. 32,847, filed Apr. 24, 1979, wherein a tri(dialkylamino)phosphine or an alkyl ester of an ortho-phosphorus acid bis(dialkylamide) is reacted with a dihalocarbene generator and the resulting product is reacted with alkyl 2-formyl-3,3-dimethylcyclopropylacetate; the resulting alkyl 2-(2,2-dihalovinyl)-3,3-dimethylcyclopropylacetates are hydrolyzed, for example, as described in "Methoden der organischen Chemie" (Houben-Weyl), Volume VIII (1952), pages 418–23 and 638–9, to the corresponding acid and the hydroxyl group of said acid is converted to an alkyl group using an alkyl metal compound, for example, as described in "Methoden der organischen Chemie" (Houben-Weyl), Volume VIII/2a (1973), pages 586–8, with subsequent hydrolysis of the addition compound formed; this resulting cyclopropylacetone is oxidized to an ester, for example, as described in "Methoden der organischen Chemie" (Houben-Weyl), Volume VIII (1952), pages 559–60 and Volume VII/2b (1976), pages 1984–6, which ester on hydrolysis yields the corresponding cyclopropylmethanol derivative, this cyclopropylmethanol derivative is oxidized to the corresponding cyclopropylcarboxylic acid, i.e., 2-(2,2-dihalovinyl)-3,3-dimethylcyclopropanecarboxylic acid, via the aldehyde, for example, as described in "Methoden der organischen Chemie" (Houben-Weyl), Volume VIII (1952), pages 407–413. These acids and reactive derivatives thereof form pyrethroid esters as described in U.S. Pat. No. 4,024,163.

The following Examples further illustrate the invention. The experiments described were carried out in a three-necked flask provided with a magnetic stirrer, a thermometer, reflux condenser, calcium chloride tube and gas inlet tube. The NMR spectra of the novel compounds were measured at 60 MHz in deuterochloroform solution relative to a tetramethylsilane standard. The yields are calculated on starting (+) 4-acetyl-2-carene, unless otherwise stated.

EXAMPLE I

A 100-ml flask was charged with (+) 4-acetyl-2-carene (30 mmol), methanol (50 ml) and sodium methoxide (33 mmol). Then, a mixture consisting of ozone and oxygen was passed through the liquid in the flask at a rate of 30 l/h (corresponding to 45 mmol of ozone per hour) while the temperature of the liquid was maintained at −70° C. After 85 min. no (+) 4-acetyl-2-carene could be detected in the reaction mixture.

After addition of dimethyl sulphide (61 mmol) to the ozonolysis product, the mixture in the flask was kept at a temperature of 65° C. for 5.7 hours. At the end of this period the solvent was evaporated, the residue formed was taken up in pentane (50 ml), the solution formed was washed with three 30-ml portions of water and the washed solution was dried over anhydrous magnesium sulphate. The solvent was evaporated from the dried solution and distillation of the residue (3.2 g) at a pressure of 1.7 kPa gave 1.5 g of a distillate boiling between 100° and 104° C., of which 93% w consisted of (+) compound B, and 0.4 g of a distillate boiling between 104° and 110° C., of which 82% w consisted of (+)

compound B. Hence, it can be calculated that the total yield of compound B was 38%.

The optical rotation of compound B $(+)_D^{20}$ was $+354.6°$ (in methanol).

EXAMPLE II

A 250-ml flask was charged with (+) 4-acetyl-2-carene (224 mmol), methanol (175 ml), potassium carbonate powder (7.2 mmol) and 3,5-di-tert-butyl-4-hydroxytoluene (4.5 mmol). Then, a mixture consisting of ozone and oxygen was passed through the liquid in the flask at a rate of 40 1/h (corresponding to 60 mmol of ozone per hour), while the temperature of the liquid was maintained between 5° C. and 10° C. After 5.5 hours no (+) 4-acetyl-2-carene could be detected in the reaction mixture.

Then, nitrogen was passed through the liquid for 3 min and a hydrogenation catalyst (0.3 g) consisting of palladium supported on carbon (10% w of palladium on carbon) was added and hydrogen of atmospheric pressure was passed through the suspension formed for 1.5 hours at a temperature of 18° C. At the end of this period the yield of compound A was 64%. Then, the catalyst was filtered off and potassium hydroxide (213 mmol) was added to the filtrate, which caused the temperature to rise to 38° C. After 1.5 hours' stirring at 20° C. a further quantity of potassium hydroxide (53 mmol) was added and stirring was continued for 30 min. The mixture formed was poured out into water (750 ml), the liquid obtained was saturated with sodium chloride and the saturated liquid was extracted with three 100-ml portions of diethyl ether. The combined extract phases were washed with two 50-ml portions of water, the washed liquid was dried over magnesium sulphate and the solvent was evaporated from the dried liquid to leave a residue (27.4 g) of which 84% w consisted of (+) compound B.

Hence, it can be calculated that the yield of (+) compound B was 64%.

It can furthermore be seen that compound A had been quantitatively converted into (+) compound B).

Acidification of the aqueous raffinate phase (obtained after the extraction with diethyl ether) with a concentrated aqueous solution of hydrochloric acid (specific gravity 1.19) until pH 4, extraction of the acidified liquid with three 50-ml portions of diethyl ether, drying of the combined extract phases over anhydrous magnesium sulphate and evaporation of the solvent from the dried liquid at a pressure of 1.7 kPa gave a residue (7.3 g) consisting of 2-formyl-3,3-dimethylcyclopropylacetic acid (3.65 g, yield 10%) and (1, R cis) homocaronic acid (2.65 g)

EXAMPLE II

A 250-ml flask as charged with (+) 4-acetyl-2-carene (100 mmol), methanol (75 ml), potassium carbonate powder (0.72 mmol) and 2,2-di(3,5-di-tert-butyl-4-hydroxyphenyl)propane (0.22 mmol). Then, a mixture consisting of ozone and oxygen was passed through the liquid in the flask at a rate of 40 1/h (corresponding to 60 mmol of ozone per hour), while the temperature of the liquid was maintained between 12° and 15° C. After 2.2 hours no (+) 4-acetyl-2-carene could be detected in the raction mixture.

Then, nitrogen was passed through the liquid for 3 min., a hydrogenation catalyst (0.3 g) consisting of palladium supported on carbon (10% w of palladium on carbon) was added and hydrogen of atmospheric pressure was passed through the suspension formed for 1.75 hours at a temperature of 15° C. At the end of this period the yield of compound A was 64%. Then sodium methoxide (204 mmol) was added and the mixture obtained was stirred for 16 hours at 20° C. At the end of this period no compound A could be detected in the mixture; compound B in its (+) configuration was present in an amount corresponding to a yield of 64%. Hence, compound A had been quantitatively converted into the (+) configuration of compound B.

2,2-Di(3,5-di-tert-butyl-4-hydroxyphenyl)propane (0.22 mmol) was added to the suspension obtained in Section (1) and a mixture consisting of ozone and oxygen was passed through at a rate of 40 l/h (corresponding to 60 mmol of ozone per hour), while the temperature was maintained between 5° and 10° C. After 1.83 hours no compound B could be detected in the reaction mixture.

Then, nitrogen was passed through the suspension for 3 min and hydrogen of atmospheric pressure was passed through for 1.75 hours at a temperature of 15° C.

At the end of this period the catalyst was filtered off, water (300 ml) was added to the filtrate and the mixture obtained was extracted with three 50-ml portions of dichloromethane to yield three organic extract phases and an aqueous raffinate phase. The combined three organic extract phases were extracted, until pH 7, with a saturated aqueous solution of sodium hydrogen carbonate to give an aqueous extract phase and an organic raffinate phase.

The combined two aqueous raffinate phases were acidified with concentrated aqueous hydrochloric acid (sp. gr. 1.19) until pH 4. The acidified mixture was extracted with three 50-ml portions of dichloromethane, the combined extract phases were dried over anhydrous magnesium sulphate and the solvent was evaporated from the dried organic liquid at 2 kPa to leave a residue (6.6 g) containing 50% 1R,cis compound C (yield 28%).

The NMR spectrum of compound C showed the following absorptions:

| | | $\delta$, ppm | | | $\delta$, ppm |
|---|---|---|---|---|---|
| $H_3C—C—CH_3$ | 6H singlet | 1.29 | $HC—CH_2—C(O)$ | 2H doublet | 2.87 |
| $H—C—CH_2$ | 1H multiplet | 1.79 | $H—C—C(O)H$ | 1H doublet | 9.82 |
| $H—C—C(O)H$ | 1H double douoblet | 1.90 | $—C(O)OH$ | 1H broad singlet | 10.4 |

The organic raffinate phase was dried over anhydrous magnesium sulphate and the solvent was evaporated from the dried organic liquid at a pressure of 2 kPa to leave a residue (1.5 g) containing 70% w methyl ester of 1R, cis compound C (yield 6.2%). The content of compound D in the residue was 15% w (yield 1.2%).

The NMR spectrum of the methyl ester of 1R, cis compound C showed the following absorptions:

|  | δ, ppm |  |  | δ, ppm |
|---|---|---|---|---|
| H₃C—C—CH₃ | 6H singlet | 1.28 | —C(O)OCH₃ 3H singlet | 3.70 |
| H—C—C(O)H and | 2H multiplet | 1.88 | H—C—C(O)H 1H doublet | 9.72 |
| H—C—CH₂ |  |  |  | J=3Hz |
| —CH—CH₂—C(O) | 2H doublet | 2.78 | J=7Hz |  |

The NMR spectrum of compound D showed the following absorptions:

|  | δ, ppm |  |  | δ, ppm |
|---|---|---|---|---|
| H₃C—C—CH₃ | 3H singlet | 1.24 | H₃C—C(O) 3H singlet | 2.34 |
|  | 3H singlet | 1.32 |  |  |
| H—C—CH₂ | 1H multiplet | 1.69 | C(O)—CH₂ 2H doublet | 3.22 |
| H—C—C(O)H | 1H double doublet | 1.93 | H—C(O)—CH 1H doublet | 9.8 |

EXAMPLE IV

A 250-ml flask was charged with (+) compound B (136 mmol), methanol (100 ml), potassium carbonate (2.2 mmol) and 2,2-di(3,5-di-tert-butyl-4-hydroxyphenyl)propane (0.66 mmol) and a mixture consisting of ozone and oxygen was passed through the liquid in the flask at a rate of 40 l/h (corresponding to 78 mmol of ozone per hour) while the temperature of the liquid was maintained between 0° and 15° C. After 1.75 hours no compound B could be detected in the reaction mixture.

Then, nitrogen was passed through the liquid for 3 min, a hydrogenation catalyst (0.3 g) consisting of palladium supported on carbon (10% w of palladium on carbon) was added and hydrogen of atmospheric pressure was passed through the suspension formed for 2 hours at a temperature of 20° C.

At the end of this period the catalyst was filtered off, the solvent was evaporated from the filtrate at a pressure of 2 kPa and the residue formed was taken up in dichloromethane (50 ml). The solution formed was washed, until pH 7, with an aqueous solution of sodium bicarbonate to yield an organic raffinate phase and an aqueous extract phase. The aqueous extract phase was acidified with concentrated aqueous hydrochloric acid (specific gravity 1.19) until pH 4. The acidified mixture was extracted with three 25-ml portions of diethyl ether, the combined extract phases were dried over anhydrous magnesium sulphate and the solvent was evaported from the dried organic liquid at a pressure of 2 kPa to leave a residue (8.4 g) containing 70% 1R, cis compound C (yield 27.7%) and 30% 1R cis homocaronic acid (yield 10.8%).

The organic raffinate phase was dried over anhydrous magnesium sulphate and the solvent was evaporated from the dried organic liquid at a pressure of 2 kPa to leave a residue (11.95 g) containing 20% w methyl ester of 1R, cis compound C, (yield 10%), and 10% w compound D (yield 5%).

EXAMPLE V

A 100-ml flask was charged with (+) compound B (19 mmol), methanol (50 ml), potassium carbonate powder (0.50 mmol) and 3,5-di-tert-butyl-4-hydroxytoluene (0.38 mmol). Then, a mixture consisting of ozone and oxygen was passed through the liquid in the flask at a rate of 40 l/h (corresponding to 78 mmol of ozone per hour) whilst the temperature of the liquid was maintained between −30° C. and −35° C. After 15 min no compound B could be detected in the reaction mixture. Then, nitrogen was passed through the liquid for 3 min, a hydrogenation catalyst (50 mg) consisting of palladium supported on carbon (10% w of palladium on carbon) was added and hydrogen of atmospheric pressure was passed through the suspension formed for 1.5 hours at at temperature of 20° C. At the end of this period the catalyst was filtered off, the solvent was evaporated from the filtrate at a pressure of 2 kPa, the residue was taken up in dichloromethane (50 ml) and the solution formed was washed with a saturated aqueous solution of sodium hydrogen carbonate to give a washed organic liquid and a spent aqueous washing solution. The washed organic liquid was dried over anhydrous magnesium sulphate and the solvent was evaporated from the dried organic liquid at a pressure of 2 kPa to leave a residue (2.95 g) containing more than 50% w compound D (yield more than 43%, calculated on starting compound B).

The spent aqueous washing solution was acidified with concentrated aqueous hydrochloric acid until pH 4 and the acidified mixture was extracted with three 10-ml portions of dichloromethane. The combined extract phases were dried over anhydrous magnesium sulphate and the solvent was evaporated from the dried organic liquid at 2 kPa to leave a residue (0.3 g) containing 85% w compound C. Hence, the yield of compound C was 8.6%, calculated on starting compound B. The balance of the residue consisted of methyl 2-carboxymethyl-3,3-dimethylcyclopropanecarboxylate (1.3% on starting compound B).

We claim:

1. A process for the preparation of 3-acetyl-6,6-dimethylbicyclo[3.1.0]-2-hexene, which comprises contacting 2-(2-acetyl-3-oxobutyl)-3,3-dimethylcyclopropanecarbaldehyde with a base selected from alkali metal hydroxides, alkali metal alkoxides, alkaline earth metal hydroxides, tertiary amines, quaternary ammonium bases and basic ion exchangers in the presence of a solvent.

2. A process according to claim 1, in which the base is an alkali metal hydroxide.

3. A process according to claim 1, in which the base is an alkali metal alkoxide with fewer than five carbon atoms per molecule.

4. A process according to claim 3, in which the base is an alkali metal methoxide.

5. A process according to claim 2, in which the alkali metal is sodium or potassium.

6. A process according to claim 1 which is carried out in the presence of an alkanol as a solvent.

7. A process according to claim 6, in which the solvent is methanol.

8. A process according to claim 1, which is carried out at a temperature in the range of from 0° C. to 125° C.

9. A process according to claim 8, which is carried out at ambient temperature.

10. A process according to claim 1 wherein the reactant aldehyde and resultant bicyclohexene are each in the (lR,cis) isomer form.

11. A process according to claim 1 in which 2-(2-acetyl-3-oxobutyl)-3,3-dimethylcyclopropanecarbaldehyde has been prepared by ozonolysis of 4-acetyl-2-carene followed by reductive cleavage of the ozonolysis product thus obtained in the presence of a reducing agent and which process is carried out in the same reaction zone or vessel as the said ozonolysis and reductive cleavage.

12. A process according to claim 11, which is carried out in the same solvent as the ozonolysis and the reductive cleavage.

13. A process according to claim 11, in which the base is already present during the ozonolysis and the reductive cleavage.

14. A process according to claim 11, in which the ozonolysis is carried out in the presence of an antioxidant which is a sterically hindered phenol having one or two ortho substituents selected from isopropyl, tert-butyl, tert-pentyl, cyclohexyl, norbornyl and isobornyl groups.

15. A process according to claim 14, in which the sterically hindered phenol is polynuclear.

16. A process according to claim 15, in which the polynuclear phenol is 2,2-di-(3,5-di-tert-butyl-4-hydroxyphenol)propane.

17. A process according to claim 14, in which the sterically hindered phenol is 3,5-di-tert-butyl-4-hydroxytoluene.

18. A process according to claim 14 in which the anti-oxidant is present in an amount in the range of from 0.001 to 10% m, based on the starting amount of 4-acetyl-2-carene.

19. A process according to claim 14, in which the ozonolysis is carried out at a temperature in the range of from −20° C. to +20° C.

20. A process for the preparation of 2-formyl-3,3-dimethylcyclopropylacetic acid, which comprises ozonolysis of 3-acetyl-6,6-dimethylbicyclo[3.1.0]-2-hexene followed by reductive cleavage in the presence of a reducing agent of the ozonolysis product thus formed.

21. A process according to claim 20, in which the ozonolysis is carried out at a temperature in the range of from −25° C. to +30° C.

22. A process according to claim 21, in which the ozonolysis is carried out at a temperature in the range of from −5° C. to +20° C.

23. A process according to claim 20 in which the ozonolysis is carried out in the presence of an antioxidant which is a sterically hindered phenol having one or two ortho substituents selected from isopropyl, tert-butyl, tert-pentyl, cyclohexyl, norbornyl and isobornyl groups.

24. A process according to claim 23, in which the sterically hindered phenol is polynuclear.

25. A process according to claim 24, in which the polynuclear phenol is 2,2-di(3,5-di-tert-butyl-4-hydroxyphenol)propane.

26. A process according to claim 23, in which the sterically hindered phenol is 3,5-di-tert-butyl-4-hydroxytoluene.

27. A process according to claim 24, in which the antioxidant is present in an amount in the range of from 0.001 to 10% m, based on the starting amount of 3-acetyl-6,6-dimethylbicyclo[3.1.0]-2-hexene.

28. A process according to claim 20, which is carried out in the presence of an alkanol as a solvent.

29. A process according to claim 28, in which the alkanol is methanol.

30. A process according to claim 28 which is carried out in the presence of a compound preventing acetal formation selected from alkali metal carbonates, alkali metal hydroxides, alkali metal alkoxides, alkaline earth metal hydroxides, tertiary amines, quaternary ammonium bases and basic ion exchangers.

31. A process according to claim 30, in which the compound preventing acetal formation is an alkali metal carbonate.

32. A process according to claim 20 in which the starting 3-acetyl-6,6-dimethylbicyclo[3.1.0]-2-hexene has been prepared by ozonolysis of 4-acetyl-2-carene, reductive cleavage of the resultant ozonolysis product in the presence of a reducing agent with formation of 2-(2-acetyl-3-oxobutyl)-3,3-dimethylcyclopropanecarbaldehyde and contacting of the latter compound with a base in the presence of solvent with formation of 3-acetyl-6,6-dimethylbicyclo[3.1.0]-2-hexene, all of these reactions being carried out in the same reaction zone or vessel.

33. A process according to claim 32, in which all of the reactions are carried out in the presence of the same solvent.

34. A process according to claim 33, in which the solvent is an alkanol with fewer than five carbon atoms per molecule and in which a compound preventing acetal formation selected from alkali metal carbonates, alkali metal hydroxides, alkali metal alkoxides, alkali metal alkoxides, alkaline earth metal hydroxides, tertiary amines, quaternary ammonium bases and basic ion exchangers is present as well.

35. A process according to claim 34, in which the alkanol is methanol.

36. A process according to claim 34, in which the compound preventing acetal formation is an alkali metal carbonate.

37. A process according to claim 32, in which the same base is used to prevent acetal formation and effect the formation of 3-acetyl-6,6-dimethylbicyclo[3.1.0]-2-hexene.

38. A process according to claim 32, in which the ozonolysis of 4-acetyl-2-carene is carried out in the presence of an antioxidant which is a sterically hindered phenol having one or two ortho substituents selected from isopropyl, tert-butyl, tert-pentyl, cyclohexyl, norbornyl and isobornyl groups.

39. A process according to claim 38, in which the ozonolysis of 4-acetyl-2-carene and 3-acetyl-6,6-dimethylbicyclo-[3.1.0]-2-hexene are carried out in the presence of the same anti-oxidant.

40. A 2-formyl-3,3-dimethylcyclopropylacetic acid, or an alkyl ester thereof.

41. A 2-formyl-3,3-dimethylcyclopropylacetic acid alkyl ester in which each alkyl group contains from 1 to 4 carbon atoms.

42. An alkyl ester according to claim 41 wherein the alkyl group is a methyl group.

43. An acid or alkyl ester according to claims 40, 41 or 42 in the (1R,cis) isomer configuration.

* * * * *